United States Patent [19]

Ohata et al.

[11] Patent Number: 4,565,823

[45] Date of Patent: Jan. 21, 1986

[54] MEDICAL AGENT FOR SUPPRESSING ARTERIOSCLEROSIS

[75] Inventors: Isao Ohata, Saitama; Nobuo Sakamoto, Chiba, both of Japan

[73] Assignee: Yamanouchi Pharmaceutical Co., Ltd., Tokyo, Japan

[21] Appl. No.: 507,024

[22] Filed: Jun. 23, 1983

[30] Foreign Application Priority Data

Jul. 2, 1982 [JP] Japan .................................. 57-114946

[51] Int. Cl.$^4$ .................................................. A61K 31/44
[52] U.S. Cl. ...................................... 514/356; 514/824
[58] Field of Search .......................................... 424/263

[56] References Cited

U.S. PATENT DOCUMENTS

| | | | |
|---|---|---|---|
| 4,150,119 | 4/1979 | Lalinde | 424/144 |
| 4,343,789 | 8/1982 | Kawata et al. | 424/32 |
| 4,404,183 | 9/1983 | Kawata et al. | 424/19 |

OTHER PUBLICATIONS

Chemical Abstracts; vol. 87; (1977), #127576u; Seki et al., Pharmacological Evaluation of YC-93, "A New Vasodilator, in Healthy Volunteers".
Chemical Abstracts; vol. 91; (1979), #168498w; Takenaka et al.
Chemical Abstracts; vol. 82; (1975) #4131j; Murakami et al.
Life Sciences, vol. 32, pp. 557–563; DeFeudis, "Calcium-Antagonists" and Atherosclerosis-Basic Studies and Therapeutic Implications (1983).
Laboratory Investigation, vol. 49, No. 2, pp. 154–158; Ginsburg et al.; "Calcium Antagonists Suppress Atherogenesis . . . " (1983).
Chemical Abstracts vol. 95, (1981); 275e; Michic et al.
Chemical Abstracts vol. 98 (1983); 141330t; Takahashi et al.

*Primary Examiner*—Leonard Schenkman
*Assistant Examiner*—Joseph A. Lipovsky
*Attorney, Agent, or Firm*—Burgess, Ryan & Wayne

[57] ABSTRACT

A medical agent for suppressing arteriosclerosis or a hypolipemic agent comprising a composition containing nicardipine or a pharmaceutically acceptable salt thereof as the effective component.

6 Claims, 1 Drawing Figure

MEDICAL AGENT FOR SUPPRESSING ARTERIOSCLEROSIS

DETAILED DESCRIPTION OF THE INVENTION

Figure 1:
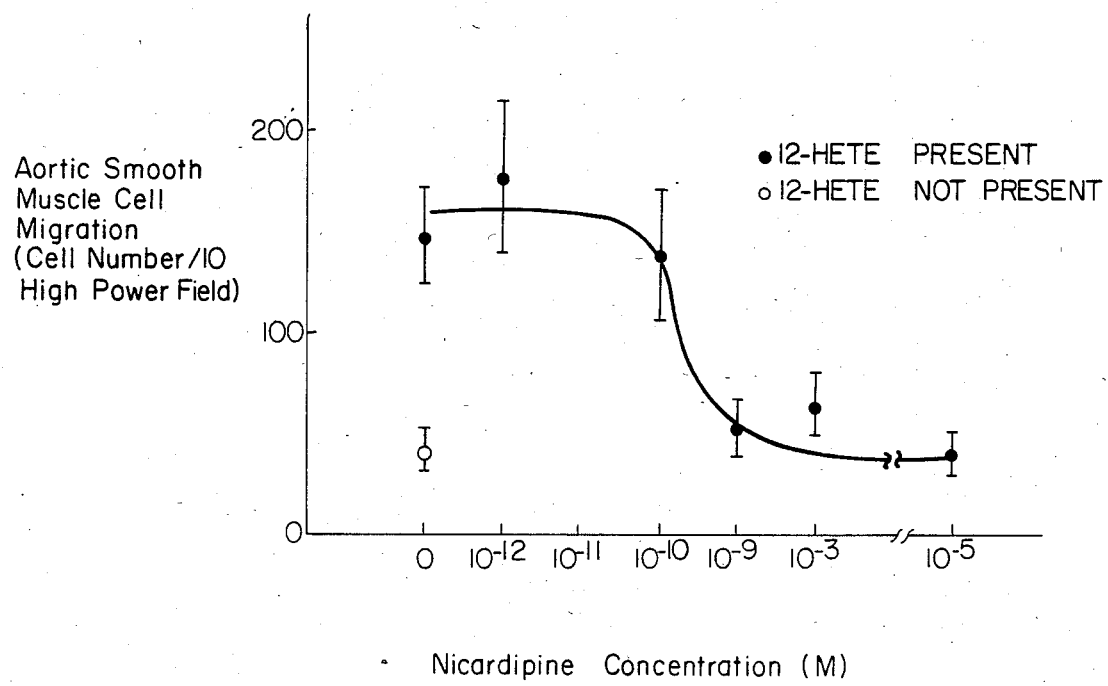

The invention relates to a medical agent for suppressing arteriosclerosis or a hypolipemic agent comprising a composition containing nicardipine (chemical name: 2,6-dimethyl-4-(3'-nitrophenyl)-1,4-(dihydropyridine-3,5-dicarboxylic acid-3-methyl ester-5-$\beta$-(N-benzyl-N-methylamino)ethyl ester. Nicardipine possesses a coronary dilator activity and a cerebral vascular dilator activity, and is a medicament useful for curing cerebral vascular desease, hypertension, and angina pectoris. The hydrochloric acid salt thereof has been already used for a medical treatment as an agent useful for the treatment of the disorder of cerebral blood flow, particularly postapoleptic conditions from cerebral hemorrhage and from cerebral embolism, etc., and hypertension.

The chemical structure of nicardipine (hydrochloride) is as follows:

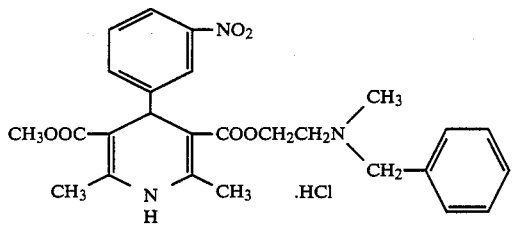

(I)

The physico-chemical characteristics of nicardipine or the salt thereof and the details about the preparation method thereof have been already disclosed in Japanese unexamined patent publication Nos. Sho 55-45075 and Sho 56-6417.

Under the circumstances, the inventors of this application have found that the compound of formula (I) unexpectedly possesses a very strong activity useful for the treatment of lipid metabolism disorder. That is, nicardipine or the salt thereof has an effect of reducing cholesterol level increased in the serum, and in addition has an effect of elevating high density lipoprotein (HDL) selectivity.

Thus, the compound used in this invention, as a hypolipemic agent, has an effective activity for the medical treatment of hyperlipidemia, arteriosclerosis and corpulence, and of metabolism disorder induced by such symptoms.

Further, nicardipine inhibits 12-HETE-associated aortic smooth muscle cell migration (aortic smooth muscle cell migration induced by 12-L-hydroxy-5,8,10,14-eicosotetraenoic acid) significantly. The migration of aortic smooth muscle cell is considered to be a main cause of progressing arteriosclerosis such as atherosclerosis. So, the above inhibition activity of nicardipine makes its indication for a medical treatment of arteriosclerosis further advantageous.

In the specification of Japanese unexamined patent publication No. Sho 56-92865, activity of improving the lipid metabolism disorder is described as to certain substituted-2-amino-3,4-dihydropyridine compounds. Meanwhile, the specification of the above publication has the description to the effect that such activity had not been known so far as to any dihydropyridine type compounds.

Nicardipine used in this invention is the other type 1,4-dihydropyridine compound different from known dihydropyridine compounds disclosed in the above publication in view of the chemical structure. Further, cholesterol reducing activity in addition to activity of increasing HDL selectively found now by this invention has not been described at all in the above publication.

The hypolipemic action of nicardipine hydrochloride is compared to that of clofibrate (conventional typical hypolipemic agent) and the results are shown in the following tables.

| Group | Administration dose (mg/kg) | Effect on cholesterol levels in the serum | | | |
|---|---|---|---|---|---|
| | | T. chol. (mg/dl) | HDL chol. (mg/dl) | LDL + VLDL chol. (mg/dl) | HDL chol. / LDL + VLDL chol. |
| | | (normal rats) | | | |
| Control | — | 50.0 ± 3.3 | 31.5 ± 3.3 | 18.5 ± 2.3 | 1.703 |
| clofibrate | 50 | 42.7 ± 2.3 | 26.5 ± 2.5 | 14.5 ± 1.0 | 1.828 |
| | 100 | 39.7 ± 2.7 | 30.3 ± 3.1 | 9.3 ± 1.5* | 3.258 |
| | 200 | 36.5 ± 4.4* | 22.8 ± 2.7 | 13.7 ± 2.1 | 1.664 |
| Nicardipine hydro-chloride | 10 | 39.4 ± 2.0* | 29.6 ± 1.4 | 9.8 ± 1.9* | 3.020 |
| | 30 | 41.3 ± 4.7 | 37.2 ± 2.7 | 3.4 ± 1.6** | 10.941 |
| | 100 | 40.8 ± 5.9 | 39.8 ± 4.3 | 2.8 ± 1.2** | 14.214 |
| | | (hyperchlolesterinemia rats) | | | |
| Control | — | 455.2 ± 54.2 | 14.8 ± 1.0 | 441.0 ± 54.6 | 0.033 |
| clofibrate | 50 | 412.0 ± 77.8 | 13.8 ± 1.0 | 379.6 ± 92.6 | 0.036 |
| | 100 | 231.0 ± 54.2 | 21.0 ± 2.5 | 210.4 ± 55.8 | 0.100 |
| | 200 | 317.4 ± 64.4 | 19.3 ± 2.8 | 298.0 ± 66.2 | 0.065 |
| Nicardipine hydro-chloride | 10 | 326.4 ± 52.0 | 27.0 ± 1.8** | 299.4 ± 52.8 | 0.090 |
| | 30 | 448.6 ± 52.8 | 28.0 ± 0.5** | 420.6 ± 53.2 | 0.067 |
| | 100 | 246.0 ± 24.6 | 47.0 ± 1.8 | 188.0 ± 26.4** | 0.250 | t — test
*$P<0.05$
**$P<0.01$
T. chol.: Total cholesterol
HDL chol.: High density lipoprotein cholesterol
LDL chol.: Low density lipoprotein cholesterol
VLDL chol.: Very low density lipoprotein cholesterol As apparent from the above table, nicardipine hydrochloride increases selectively HDL chol (cholesterol of high density lipoprotein), and in addition reduces remarkably LDL chol (cholesterol of low density lipoprotein) in hypercholesterolemia rats, so it has become possible to reduce the amount of total cholesterol in the serum.

It is considered at present that it is important that the agent used for improving lipid metabolism disorder has serum cholesterol reducing activity and at the same time has HDL chol increasing activity, so nicardipine hydrochloride is considered to be a new type of agent for improving lipid metabolism disorder different from clofibrate from the viewpoint of the activity.

Nicardipine hydrochloride is a low toxicity compound, and this fact is confirmed by acute toxicity examination experiment. The result of the examination is shown in the following table, as $LD_{50}$(mg/kg) values.

| Drugs | Administration route | mice (ICR) male | mice (ICR) female | rats (Wister) male | rats (Wister) female | rats (S.D.) male | rats (S.D.) female | dog (mongrel) |
|---|---|---|---|---|---|---|---|---|
| Nicardipine hydrochloride | i.v. | 20.7 (18.7–22.9) | 19.9 (17.5–22.5) | 15.5 (13.1–18.2) | 17.2 (15.1–19.5) | 18.1 (16.6–19.7) | 25.0 (23.3–26.7) | (5.0–8.1) |
| | p.o. | 634 (526–767) | 650 (539–787) | 187 (155–223) | 184 (152–225) | 643 (543–759) | 557 (444–736) | 60<MLD |
| | s.c. | 540 (461–631) | 710 (643–826) | 677 (541–919) | 606 (486–798) | — | — | |
| papaverine | i.v. | 27.0 (24.1–30.1) | — | 13.3 (11.3–15.6) | — | — | — | | numerical figures in parentheses: 95% confidence limit
i.v.: intravenous route;
p.o.: peroral route
s.c.: subcutaneous route.

The administration dose of nicardipine or the salt thereof in case of using it as medical agent for suppressing arteriosclerosis or hypolipemic agent is usually 10–500 mg a day by single dose per an adult (preferably about 50–100 mg) in a case of oral administeration, judging from some experiments in animals.

Various formulations such as tablets, powders, capsules, granules, etc. may be used in case of the oral administration, and any of such formulations can be adopted. Such formulations can be prepared in a conventional manner using additives for formulations generally used such as calcium carbonate, corn starch, talc, magnesium stearate, lactose, etc.

Further, the compound used in this invention can be also administered as an aqueous or oily liquid agent or suspension agent.

The details of the experiment of examining the hypolipemic activity of the compound used in this invention are shown below.

Male Sprague-Dawley rats (JCL ®, Nippon Clea Co. Ltd., Tokyo, Japan) weighing 90–100 g were fed semipurified diet containing 10% coconut oil, 1.5% cholesterol and 0.5% cholic acid. Three days after the start of feeding, the rats are allocated at random by the body weight to multiple groups each consisting 6–8 rats. On day 4 through 7, the drug suspension in 0.5% methylcellulose was orally given daily. The control group received a comparable volume of vehicle. Following the final dose, the rats were fasted overnight (approximately 16 hours). Under ethylether anesthesia, blood was taken from the inferior vena cava. Serum was obtained by centrifugation at 1,600 xg for 15 min and stored at 4° C. in plastic tubes. The amount of total cholesterol and HDL cholesterol in the serum were determined. The determination of the total cholesterol was practiced by the method described in Schettler, G & Nüssel; "Arbeitsmed. Sozialmed. Präventivmed." 10, 25 (1975) and the determination of HDL cholesterol was practiced by the method described in T. T. Ishikawa et al; "Lipids", 11, 628 (1976).

The effect of nicardipine on 12-HETE-associated aortic smooth muscle cell migration can be examined by measuring the migration of aortic smooth muscle cell by filter membrane technique in modified Boyden chambers as follows:

$5 \times 10^5$ of the smooth muscle cells were suspended in $Ca^{2+}$-containing culture medium supplemented with 5% calf serum containing various concentration of nicardipine. Control cultures contained the same volume, a final concentration of 1% (v/v), of methanol. The suspensions of the smooth muscle cells were placed in the upper compartment of the chamber. The lower compartment of the chamber contained the same culture medium supplemented with $6 \times 10^{-15}$ g/ml of 12-HETE and 5% calf serum containing no nicardipine. The cells was incubated at 37° C. As control, medium with the same concentration of solvent (1% ethanol) containing no 12-HETE was used. Smooth muscle cell migration was quantitated microscopically by counting the number of cells that migrated into the filter. In each experiment, 10 high-power fields in 5 replicate cultures were examined to determine the number of cells that had migrated into the filers. Cell migration was expressed as cells/10 HPF (high-power fields) in FIG. 1.

What is claimed is:

1. A method of suppressing arteriosclerosis in a subject having said condition which comprises:
    administering to the subject being treated an arteriosclerosis suppressing amount of a composition containing nicardipine or a pharmaceutically acceptable salt thereof and a pharmaceutically acceptable carrier.

2. The method of claim 1 wherein the salt is nicardipine hydrochloride.

3. The method of claim 1 wherein the arteriosclerosis suppressing amount comprises from about 10–500 milligrams per day of nicardipine.

4. A method of producing hypolipemic activity in a subject in need of such treatment which comprises:

administering to the subject being treated a hypolipemic activity inducing amount of a composition containing nicardipine or a pharmaceutically acceptable salt thereof and a pharmaceutically acceptable carrier.

5. The method of claim 4 wherein the pharmaceutically acceptable salt is nicardipine hydrochloride.

6. The method of claim 4 wherein the hypolipemic activity inducing amount comprises from about 10–500 milligrams per day of nicardipine.

* * * * *